United States Patent [19]

Sutton et al.

[11] Patent Number: 5,330,891

[45] Date of Patent: Jul. 19, 1994

[54] METHOD FOR DETECTION OF A NUCLEIC ACID USING PARTICULATE REAGENT HAVING POLYOXYALKYLENE SIDE CHAINS

[75] Inventors: Richard C. Sutton; Marsha B. Oenick, both of Rochester, N.Y.

[73] Assignee: Eastman Kodak Company, Rochester, N.Y.

[21] Appl. No.: 968,936

[22] Filed: Oct. 30, 1992

Related U.S. Application Data

[62] Division of Ser. No. 558,272, Jul. 25, 1990, Pat. No. 5,200,315.

[51] Int. Cl.$^5$ ............... C12Q 1/70; G01N 21/00; C08L 33/00; C08F 12/16
[52] U.S. Cl. .................................. 435/5; 435/6; 435/7.5; 435/7.92; 435/7.94; 435/7.95; 435/962; 435/969; 435/970; 435/974; 435/975; 436/518; 436/523; 436/531; 524/817; 524/825; 526/286; 526/293; 526/320; 526/346; 935/77; 935/78
[58] Field of Search ............... 526/320, 286, 293, 346, 526/329.2; 524/817, 825; 435/5, 6, 7.5, 7.9, 7.92, 7.94, 7.95, 962, 969–970, 974–975; 428/403, 407; 436/161, 518, 523, 531; 935/76-78

[56] References Cited

U.S. PATENT DOCUMENTS

| | | | |
|---|---|---|---|
| 3,983,001 | 9/1976 | Coupek et al. | 195/66 R |
| 4,144,306 | 3/1979 | Figueras | 422/56 |
| 4,304,591 | 12/1981 | Mueller et al. | 71/93 |
| 4,401,765 | 8/1983 | Craig et al. | 436/533 |
| 4,418,152 | 11/1983 | Hosaka et al. | 436/534 X |
| 4,615,983 | 10/1986 | Koyama | 436/535 X |
| 4,703,018 | 10/1987 | Craig et al. | 436/518 |
| 4,735,907 | 4/1988 | Schaeffer et al. | 436/534 |
| 4,794,090 | 12/1988 | Parham et al. | 436/534 X |
| 5,086,143 | 2/1992 | Sutton et al. | 526/320 |

FOREIGN PATENT DOCUMENTS

| | | | |
|---|---|---|---|
| 0166559 | 10/1982 | Japan | 436/534 |
| 0235061 | 10/1985 | Japan | 436/534 |

OTHER PUBLICATIONS

Nagaoka et al, Chem Ab 97(2)11787, "Interactions between biological components and hydrogels with poly(oxyethylene) chain . . . " in Kobunshi Ronbunshu, 39(4), 165–71 (1982).

Andrade et al, Chem Ab 113(12)99914, "Polymer serfactants for protein resistance . . . " in WO9003406 Apr. 5, 1990.

Primary Examiner—Carol A. Spiegel
Attorney, Agent, or Firm—J. Lanny Tucker

[57] ABSTRACT

Biologically active reagents are prepared from particles of copolymers having polyoxyalkylene side chains, each of which side chains has a molecular weight of at least about 88. The reagents are prepared by covalently attaching biologically active substances, for example antibodies, to the particles, directly or indirectly through reactive groups on the particle surface. These reagents are used to advantage in analytical elements and methods for the detection of specific binding ligands (such as immunological species) and immunoassays, and in purification methods as affinity chromatography reagents. Adsorption of undesirable proteins on the particles of the reagents was considerably reduced because of the specific composition of the particles.

9 Claims, No Drawings

METHOD FOR DETECTION OF A NUCLEIC ACID USING PARTICULATE REAGENT HAVING POLYOXYALKYLENE SIDE CHAINS

RELATED APPLICATION

This is a divisional application of Ser. No. 558,272, filed Jul. 25, 1990, U.S. Pat. No. 5,200,315.

Reference is made to copending and commonly assigned U.S. Ser. No. 557,338, filed on even date herewith by Sutton and Oenick and entitled "Copolymers Containing Polyoxyalkylene Side Chains", now U.S. Pat. No. 5,086,143.

FIELD OF THE INVENTION

The present invention relates to biologically active reagents prepared using polymeric particles. It also relates to analytical elements containing such reagents, and to immunoassays and specific binding analytical methods using them. Further, it relates to an analytical purification method using the reagents. This invention can be used for various clinical, diagnostic, medical and research purposes.

BACKGROUND OF THE INVENTION

There is a continuing need in medical practice and research, and in analytical and diagnostic procedures for rapid and accurate determinations of chemical and biological substances which are present in various fluids, such as biological fluids. For example, the presence of drugs, narcotics, hormones, steroids, polypeptides, metabolites, toxins, viruses, microorganisms or nucleic acids in human or animal body fluids or tissues must be determined rapidly and accurately for effective research, diagnosis or treatment.

In approximately the last twenty years, a wide variety of analytical methods have been developed to detect the substances noted above. Generally, the state of the art has advanced to such a degree that analytical and diagnostic methods have become highly reliable and suitable for automation or for use with test kits which can be readily used in doctors' offices or at home. Most of such methods rely on what are known in the art as "specific binding" reactions in which an unknown substance to be detected (known as a "ligand") reacts specifically and preferentially with a corresponding "receptor" molecule. Most well known specific binding reactions occur between immunoreactants, such as antibodies and antigens (foreign substances which produce immunological responses), but other specific binding reactions (such as between avidin and biotin, and a sugar with a lectin) are well known.

Methods in the art using specific binding reactions generally require that one or more or both of the reactants be immobilized on a solid substrate of some type, so that unreacted (and generally water-soluble) materials can then be separated from the water-insoluble reaction product (often called a "complex"). In addition, such immobilized reactants can be used in affinity chromatography to remove a desired biologically active material from a mixture of such materials.

Biologically active substances have thus been immobilized to advantage on particulate substrates such as polymeric particles, animal and human erythrocytes, bacterial cells and other materials known in the art. For example, carrier particles prepared from epoxy-group containing monomers are described in U.S. Pat. No. 4,415,700 (issued Nov. 15, 1983 to Batz et al). Carboxylated latex particles have also been used to prepare diagnostic reagents, as noted in U.S. Pat. No. 4,181,636 (issued Jan. 1, 1980 to Fischer). Where polymeric particles have been used as carrier substrates, biologically active substances have been attached through reactive groups on the particle surface, such groups provided either from the polymer composition or from linking moieties attached to the particles. U.S. Pat. No. 4,401,765 (issued Aug. 30, 1983 to Craig et al) describes a number of reactive groups on polymeric particles.

Several advances in the art in this regard are described in U.S. Ser. No. 081,206 (filed Aug. 3, 1987 by Sutton et al) abandoned in favor of U.S. Ser. No. 07/742,198 (filed Dec. 5, 1991), now U.S. Pat. No. 5,177,023, U.S. Ser. No. 136,165 (filed Dec. 18, 1987 by Burdick et al) and EP-A-0 308 235 (published Apr. 26, 1989 and corresponding to U.S. Ser. No. 373,304, filed Jun. 29, 1989 by Sutton et al as a continuation-in-part of U.S. Ser. No. 098,429, filed Sep. 18, 1987, now abandoned). These applications describe various means for attaching biologically active substances to polymeric particles having various reactive surface groups.

U.S. Pat. No. 3,983,001 (issued Sep. 28, 1976 to Coupek et al) describes the use of hydrophilic macroporous copolymers as carriers for biologically active compounds in the preparation of affinity chromatography reagents. Such copolymers can be prepared from certain hydrophilic monomers such as polyglycol acrylates and methacrylates. Biologically active compounds are adsorbed to the carrier polymers. Absorption, however, does not provide for optimum sensitivity or efficiency in affinity chromatography.

The modification of protein adsorption on polymeric surfaces has been a common goal for many workers trying to apply polymer technology to in vivo and in vitro uses in biotechnology. Undesirable protein adsorption has been a continual problem. For example, nonspecific adsorption is a major concern in the use of polymers for affinity chromatography for purification of proteins.

The modification of polymer surfaces has taken many forms, including physical coatings, graft copolymerization, chemical treatments and plasma gas discharge treatment. The hydrophilic nature of the polymer surface has been the subject of considerable debate and research because an increase in hydrophilicity reduces adsorption of some proteins, but not others. As noted in the art cited above, the use of reactive side chains has also received considerable attention in the art. However, if the polymer particles are too hydrophilic and swell in aqueous solutions (as in U.S. Pat. No. 3,983,001, noted above), the assays can be adversely affected.

One technique commonly used to reduce nonspecific adsorption of proteins is what is called "capping". After a desired protein (for example, an antibody) is covalently attached to polymeric particles, another nonimmunoreactive protein is allowed to adsorb to the particle surface to "cap" the remaining reactive sites. While this is generally effective in some cases, it would be desirable to avoid this step because of the expense and extra time it requires for preparing useful reagents. Thus, there is a continuing need for a means to provide biological reagents comprising polymeric particles as carriers without the need for "capping" and where nonspecific interactions are considerably reduced or eliminated entirely.

SUMMARY OF THE INVENTION

The problems noted above are overcome with a a biologically active reagent comprising:

(I) a water-insoluble, nonporous particle composed of, at least on its surface, a copolymer having recurring units derived from:
 (a) at least about 0.5 mole % of one or more ethylenically unsaturated polymerizable monomers having reactive groups which are, directly or indirectly, capable of reaction with free amine or sulfhydryl groups of biologically active substances,
 (b) from about 0.1 to about 20 mole % of one or more ethylenically unsaturated polymerizable monomers having polyoxyalkylene side chains, each of which side chains has a molecular weight of at least about 88, and
 (c) up to about 99.4 mole % of one or more ethylenically unsaturated polymerizable oleophilic monomers which provide hydrophobicity to the copolymer, and (II) a biologically active substance covalently attached to the particle through the reactive groups.

This reagent can be used in a variety of situations, including an analytical element which comprises a substrate having one or more reaction zones therein, and containing in at least one of the zones, the biologically active reagent described above.

Moreover, a method for the determination of a specific binding ligand comprises:

A. forming a water-insoluble specific binding complex of a specific binding ligand of interest, or a receptor therefor, with a reagent comprising:
 (I) a water-insoluble, nonporous particle as described above, and
 (II) a biologically active substance covalently attached to the particle through the reactive group, the substance being specifically reactive with either the ligand or a receptor therefor, and B. detecting the presence of the complex as an indication of the presence or amount of the ligand in the specimen.

This invention also provides an assay for the determination of a specific binding ligand comprising:

detecting the presence or amount of a water-insoluble specific binding complex formed between a ligand of interest and a receptor therefor, the receptor provided as a component of a reagent comprising:
 (I) a water-insoluble, nonporous particle as described above, and
 (II) the receptor for the ligand being covalently attached to the particle through the reactive group.

Still further, an immunoassay employing antibodies or antigens for detecting the presence or amount of a ligand in a specimen comprises addition of an immunoreactant which is specifically reactive with the ligand or with a receptor therefor, the immunoreactant being a component of a reagent comprising:
 (I) a water-insoluble, nonporous particle as described above, and
 (II) the immunoreactant being covalently attached to the particle through the reactive group.

An analytical separation method of this invention comprises:

A. passing a specimen containing a mixture of biologically active substances over an affinity chromatography reagent comprising:
 (I) a water-insoluble, nonporous particle as described above, and
 (II) a specific binding substance covalently attached to the particle through the reactive group, the specific binding substance being specific to one or more predetermined biologically active substances in the specimen mixture of biologically active substances to form a complex of the reagent with the one or more predetermined substances, and B. collecting either the one or more complexed predetermined substances or one or more substances remaining in the eluent.

The present invention provides reagents which are useful in a variety of analytical, diagnostic and purification methods. Moreover, nonspecific adsorption of unwanted proteins and carbohydrates on these particles is reduced and a "capping" procedure can be avoided.

These advantages are achieved with this invention by preparing the reagents with particles which are composed of a copolymer having both surface reactive groups for attaching useful biological compounds, as well as polyoxyalkylene side chains, each side chain having a molecular weight of at least about 88. These side chains extend from the particle surface to prevent unwanted protein adsorption.

DETAILED DESCRIPTION OF THE INVENTION

The copolymers useful in the preparation of the reagents of this invention and methods of preparing same are described in detail in our U.S. Ser. No. 557,338, now U.S. Pat. No. 5,086,143. The following discussion is provided as a summary of these copolymers.

The copolymers have as an essential component recurring units derived from one or more ethylenically unsaturated polymerizable monomers having polyoxyalkylene side chains of a specific molecular weight. These monomers are identified as those in the (b) component of the definition of the copolymers provided herein. A mixture of monomers can be used if desired.

Each polyoxyalkylene side chain generally has a molecular weight of from about 88 to about 1320. Such side chains can have linear or branched alkylene groups of 2 to 4 carbon atoms, and if there is more than one of such groups in a given monomer, they can be the same or different. Preferably, each monomer contains one such alkylene group.

More specifically, these monomers are represented by the structure (I):

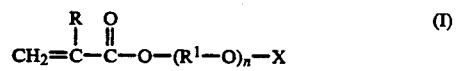

wherein R is hydrogen or methyl, and $R^1$ is alkylene having 2 to 4 carbon atoms (such as ethylene, propylene, trimethylene, n-butylene or iso-butylene). X is hydrogen or acyl (such as acetyl, propionyl, butyryl or benzoyl), and n is 2 to 30.

Preferably, R is hydrogen or methyl, $R^1$ is an alkylene having 2 or 3 carbon atoms (branched or linear), X is hydrogen and n is 2 to 20.

Representative monomers [component (b)] of the copolymer include, but are not limited to, pentaethylene glycol monomethacrylate, decaethylene glycol mono methacrylate, eicosaethylene glycol monomethacrylate, pentaethylene glycol monoacrylate, polypropylene glycol monomethacrylate and polypropylene glycol monoacrylate. The preferred monomers include pentaethylene glycol monomethacrylate, decaethylene glycol monomethacrylate and polypropylene glycol monomethacrylate, with the first two being most preferred.

The monomers described above are copolymerized with two other types of ethylenically unsaturated polymerizable monomers to provide useful copolymers.

The (a) monomers have reactive groups which are, directly or indirectly, capable of reaction with free amine or sulfhydryl groups of biologically active substances, and the (c) monomers are oleophilic to provide additional hydrophobicity to the copolymer.

There are many polymerizable monomers which have the reactive groups necessary for reaction with biologically active substances. These reactive groups can be directly reacted with the biologically active substances, or indirectly reacted through linking moieties or through intermediates which are created during attachment of the biologically active substances to the particles. A mixture of monomers having the same or different reactive groups can be used if desired.

Representative reactive groups include carboxy, active halogens, activated 2-substituted ethylsulfonyl, activated 2-substituted ethylcarbonyl, active esters, vinylsulfonyl, vinylcarbonyl, aldehyde, epoxy, amino (after activation), sulfhydryl and others which would be readily apparent to one skilled in the art. A considerable number of representative monomers are listed in our copending U.S. Ser. No. 557,338, now U.S. Pat. No. 5,086,143.

Particularly useful monomers include, but are not limited to, m & p-(2-chloroethylsulfonylmethyl)styrene, m & p-[2-(p-tolylsulfonyloxy)ethylsulfonylmethyl]styrene, m & p-vinylsulfonylmethylstyrene, N-[m & p-(2-chloroethylsulfonylmethyl)phenyl]acrylamide, and N-[2-(2-chloroethylsulfonyl)ethylformamidomethyl]acrylamide. The first monomer is one of the most preferred.

Additional particularly useful comonomers having a reactive carboxy group are described in copending U.S. Ser. No. 539,768 (filed Jun. 18, 1990 by Ponticello and Sutton), now abandoned in favor of continuation-in-part U.S. Ser. No. 07/654,112 (filed Feb. 12, 1991), now U.S. Pat. No. 5,149,737.

A summary of those particularly useful monomers follows, with the understanding that further details would be readily apparent to a skilled polymer chemist, and details of their preparation and use are noted in the copending Ponticello and Sutton application, noted above.

In general, the ethylenically unsaturated polymerizable monomers having reactive carboxy groups have the following structure (II):

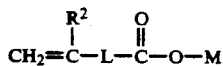
II wherein $R^2$ is hydrogen, halo or alkyl of 1 to 3 carbon atoms, M is hydrogen, an alkali metal ion or an ammonium ion and L is an organic linking group having from 8 to 50 carbon, oxygen, nitrogen or sulfur atoms in the linking chain. A mixture of monomers can be used if desired.

More specifically, in Structure II, $R^2$ is hydrogen, halo (such as chloro or bromo) or alkyl of 1 to 3 carbon atoms (such as methyl, ethyl, isopropyl and n-propyl. More preferably, $R^2$ is hydrogen or methyl.

Also, M is hydrogen, an alkali metal ion (such as lithium, sodium and potassium) or an ammonium ion (such as ammonium, tetramethylammonium and tetraethylammonium). Preferably, M is hydrogen or an alkali metal ion, and more preferably, it is hydrogen or sodium.

L is an organic linking group which has from 8 to 50 of a combination of carbon, nitrogen, oxygen or sulfur atoms in the chain. The linkage comprises two or more divalent hydrocarbon groups such as alkylene, arylene, alkylenearylene, arylenealkylene and similar groups which are connected or terminated with the noted heteroatoms or with heteroatom-containing groups such as carbonyl, sulfonyl, imino and others known in the art. Such hydrocarbon groups can have from 1 (such as methylene) up to 12 carbon atoms, and can be branched, linear or cyclical, substituted or unsubstituted with one or more alkyl groups (preferably of from 1 to 12 carbon atoms, such as methyl, ethyl, isopropyl, hexyl and octyl), alkoxy (preferably from 1 to 12 carbon atoms, such as methoxy, ethoxy, propoxy, t-butoxy and octyloxy), cycloalkyl (preferably from 4 to 6 carbon atoms, such as cyclobutyl, cyclohexyl and cyclopentyl), aryl (preferably from 6 to 12 carbon atoms, such as phenyl, tolyl, xylyl, naphthyl, 4-methoxyphenyl and chlorophenyl). Such groups are not difficult to design or synthesize for one skilled in synthetic chemistry.

Preferably, L comprises two or more alkylene arylene or arylenealkylene groups which are connected or terminated with an oxy, thio, imino ($-NR^3-$), carbonyloxy ($-COO-$), carbonylimino ($-CONR^3-$), ureylene ($-NR^3CONR^3-$) or sulfonylimino ($-SO_2N-R^3-$) group, wherein each $R^3$ in the noted groups is independently hydrogen, alkyl having 1 to 10 carbon atoms (such as methyl, ethyl, isopropyl, n-butyl, hexyl, benzyl and 2,4-dimethylpentyl), cycloalkyl having 4 to 10 carbon atoms in the backbone (such as cyclopentyl, cyclohexyl and 1,3-dimethylcyclohexyl) or aryl having 6 to 14 carbon atoms in the backbone (such as phenyl, xylyl, p-chlorophenyl, naphthyl and anthryl).

Representative L groups include, but are not limited to:

p-phenylenemethyleneoxycarbonyltrimethylene, carbonyloxyethyleneoxycarbonyltrimethylene, carbonyloxyethyleneureylenepentamethylene, carbonylpenta(oxyethylene)oxycarbonyltrimethylene, carbonyldeca(oxyethylene)oxycarbonyltrimethylene, p-phenylenemethylenethioethyleneoxycarbonyltrimethylene, carbonyloxyethyleneiminocarbonyltrimethylene, carbonyloxytetramethyleneoxycarbonyltetramethylene, p-phenylenemethyleneiminocarbonyltrimethylene, p-phenylenemethyleneiminocarbonyltrimethylene, p-phenylene(methyl)iminoethyleneoxycarbonyltrimethylene, p-phenylenemethylenethioethylene, p-phenylenemethylenethioethyleneiminocarbonylmethyleneoxymethylene, p-phenylenemethylenethioethyleneiminocarbonylmethylenethiomethylene, p-phenylenemethylenethioethyleneiminocarbonyltrimethylene, phenylenemethylenethio-1-carboxyethylene, phenylenemethylenethiophenylene, phenylenemethylenethioethyleneoxyethylenethiomethyleneoxycarbonylethylene, phenylenemethyleneoxyphenylenemethylenethioethylene, phenylenemethylenethioethyleneoxyethylenethioethyleneoxycarbonylethylene, phenylenemethyleneoxyphenylenemethylenethiophenylenemethylenethiotrimethylene and phenylenemethylenethioethyleneoxyethylenethioethyleneoxycarbonylphenylene.

Representative monomers described by Structure II include, but are not limited to: mono-m & p-vinylbenzyl glutarate, mono-p-vinylbenzyl glutarate, mono-2-methacryloyloxyethyl glutarate, 2-(4-carboxybutyramido)ethyl methacrylate, 2-[N'-(5-carboxypentyl)ureido]ethyl methacrylate, mono-methacryloylpenta(oxyethylene) glutarate, mono-(4-acryloyloxybutyl) glutarate, 4-(4-carboxybutyramido)styrene, mono-methacryloyldeca(oxyethylene) glutarate, mono-2-(p-vinylbenzylthio)ethyl glutarate, mono-2-(m- & p-vinylbenzylthio)ethyl glutarate, 4-(4-carboxybutyramidomethyl)styrene, mono-2-[N-methyl-N-(4-vinylbenzyl)amino]ethyl glutarate, 3-(p-vinylbenzylthio)propionic acid, 4-[2-(4-carboxybutyramido)ethylthiomethyl]styrene, 4-[2-(carboxymethoxyacetamido)ethylthiomethyl]styrene, 4-[2-(carboxymethylthioacetamido)ethylthiomethyl]styrene, mono-2-(4-vinylbenzylthio)ethyl succinate, 4-[2-(carboxymethoxyacetoxy)ethylthiomethyl]styrene, mono-4-vinylbenzyl succinate, 2-(4-vinylbenzylthio)succinic acid, 2-(4-vinylbenzylthio)benzoic acid, mono-2-[2-(4-vinylbenzylthio)ethoxy]ethylthiomethyl malonate, mono-methacryloylpenta(oxyethylene) phthalate, mono-methacryloyldeca(oxyethylene) phthalate, mono-2-{2-[2-(4-vinylbenzylthio)ethoxy]ethylthio}ethyl succinate, mono-2-{2-[2-(4-vinylbenzylthio)ethoxy]ethylthio}ethyl phthalate, 3-[4-(4-vinylbenzyloxy)benzylthio]propionic acid and 4-{4-[4(4-vinylbenzyloxy)benzylthio]benzylthio}butyric acid.

In addition to the (a) and (b) monomers described above, the copolymers also include recurring units of ethylenically unsaturated polymerizable oleophilic monomers (c) which provide desired additional hydrophobicity to the copolymers. Such monomers include, but are not limited to, vinyl aromatics (for example, styrene and styrene derivatives such as 4-vinyltoluene, α-methylstyrene, 2,5-dimethylstyrene, 4-t-butylstyrene and 2-chlorostyrene), acrylic and methacrylic acid esters and amides (for example, methyl acrylate, methyl methacrylate, n-butyl acrylate, 2-ethylhexyl methacrylate, benzyl acrylate and N-phenylacrylamide), butadiene, acrylonitrile, vinyl acetate, vinylbenzyl acetate, vinyl bromide, vinylidene chloride and crosslinkable monomers having two or more polymerizable groups. Useful crosslinkable monomers include, but are not limited to divinylbenzene, allyl acrylate and di- and triacrylates and methacrylates (for example 2,2-dimethyl-1,1,3-propylene diacrylate, 1,4-cyclohexylenedimethylene dimethacrylate, ethylidyne trimethacrylate, ethylene diacrylate, ethylene dimethacrylate, propylene diacrylate and propylene dimethacrylate) and others readily apparent to one skilled in polymer chemistry. A mixture of monomers can be used if desired.

The copolymer useful in this invention is composed of recurring units derived from the monomers (a), (b) and (c) identified herein in the following molar amounts:

one or more (a) monomers of at least about 0.5 mole percent, one or more (b) monomers of from about 0.1 to about 20 mole percent, and one or more (c) monomers of up to about 99.4 mole percent.

Preferably, there are derived recurring units of from about 1 to about 20 mole % of (a), from about 1 to about 20 mole % of (b), and from about 60 to about 98.5 mole % of (c). Most preferred copolymers are prepared from about 1 to about 10 mole % of (a), from about 1 to about 10 mole % of (b), and from about 80 to about 98 mole % of (c).

The copolymers of this invention are prepared using standard emulsion or suspension polymerization techniques, as described for example by Sorenson et al in *Preparative Methods of Polymer Science*, 2nd Ed. (1968), Wiley and Sons, New York, and Stevens, *Polymer Chemistry, An Introduction*, Addison Wesley Publishing Co., London, 1975, and certain preferred conditions are discussed in our copending U.S. Ser. No. 557,338, now U.S. Pat. No. 5,086,143.

The reagents of this invention have one or more biologically active substances covalently attached to the polymeric particles through the reactive groups on the outer surface of the particles. As used herein, the term "biologically active substance" is meant to include any organic compound which is found in a living organism or which is useful in the diagnosis, treatment or genetic engineering of cellular material or living organisms, and which has a capacity for interaction with another biological or chemical material. Such substances may or may not be naturally occurring in biological fluids. Such materials must be capable of attaching to the particles through direct or indirect reaction with the reactive groups on the particles. Many such attachment procedures are well known.

Depending upon the intended use of the reagent, the biologically active substances can be from a wide variety of naturally occurring or synthetically prepared materials, including, but not limited to amines, enzymes, amino acids, peptides, polypeptides, proteins (including antibodies, C-reactive protein and avidin and its derivatives), lipoproteins, glycoproteins, hormones (such as thyroxine, triiodothyronine, and human chorionic gonadotropin), drugs (for example digoxin, phenytoin, phenobarbital, gentamicin, carbamazepine and theophylline), steroids, vitamins, polysaccharides, glycolipids, alkaloids, microorganisms, viruses, protozoa, fungi, parasites, rickettsia, molds, blood components, tissue and organ components, pharmaceuticals, haptens, lectins, toxins, nucleic acids (including oligonucleotides, either single- or double-stranded), antigenic materials (including proteins and carbohydrates), biotin or derivatives thereof, and components of any of the materials just listed and others known to one skilled in the art.

Particularly useful reagents of this invention are those in which the biologically active substance is a receptor molecule specific to a ligand of interest. Thus, a specific binding reaction involving the reagent can be used for various methods (described in more detail below). Examples of ligand-receptor complexes (that is, reaction of the ligand and receptor) include, but are not limited to antibody-antigen, antibody-hapten, avidin-biotin, sugar-lectin, gelatin-fibronectin and Protein A-IgG complexes. For purposes of this invention, complementary nucleic acids (that is, a hybridized product of complementary strands) are also considered specific binding materials. Such complementary nucleic acids (including oligonucleotides having at least 2 bases) need not be complementary at every base pair, nor must there be a matching base at every position in the nucleic acid sequence. That is, one of the strands can be longer than the other, or one strand can by hybridized with a plurality of oligonucleotides complementary thereto at different sequences.

Most useful biologically active substances are what are known in the art as immunological species which include: (1) any substance which, when presented to an immunocompetent host, will result in the production of a specific antibody capable of binding with that substance, or (2) the antibody so produced, which compound participates in an antigen-antibody reaction. Thus, the immunological species can be an antigenic material or an antibody (including anti-antibodies). Both monoclonal and polyclonal antibodies are useful, and they can be whole molecules or various fragments thereof, as long as they have at least one reactive site for reaction with the reactive groups on the particles, or with linking groups attached or attachable to (described below).

In certain embodiments, the immunological species is an enzyme which has a reactive group for attachment. Representative enzymes include, but are not limited to, horseradish peroxidase, glucose oxidase, urease, $\beta$-galactosidase, aspartate aminotransaminase, alanine aminotransaminase, lactate dehydrogenase, creatine phosphokinase, gamma glutamyl transferase, alkaline phosphatase, acid phosphatase and prostatic acid phosphatase.

Particularly useful biologically active substances include antibodies directed to Streptococcus A, a microorganism associated with periodontal disease, carbamazepine, thyroxine, human chorionic gonadotropin, phenobarbital, phenytoin, digoxin or C-reactive protein.

In other embodiments, such as for competitive binding assays for determination of drugs or pregnancy, the biologically active substance is an antibody directed to human chorionic gonadotropin, thyroxine, phenobarbital, phenytoin or digoxin.

If desired, the biologically active substance can be modified or chemically altered to provide reactive groups for attachment including providing a linking moiety for attachment. There is considerable technology known in the art for such chemical modification or the use of linking moieties, including teaching in such references as U.S. Pat. No. 4,914,210 (issued Apr. 13, 1990 to Levenson et al) and WO-A-89/2932 published Apr. 6, 1989) both directed to modification of oligonucleotides, U.S. Pat. No. 4,719,182 (issued Jan. 12, 1988 to Burdick et al), Erlanger et al, J.Biol.Chem., 234, 1090 (1959), Weston et al, Biochim.Biophys.Acta, 612, pp.40–49 (1980) and Borzini et al, J.Immunol.Methods, 44, pp. 323-332 (1981).

The general procedure for preparing the reagent of this invention is as follows: the polymer particles are mixed with the biologically active substance in an aqueous buffered solution (pH generally from about 5.5 to about 8.5). The % solids of particles is generally from about 0.01 to about 10%, and preferably from about 0.1 to about 3%. The amount of biologically active substance is generally designated by a weight ratio of substance to polymer of from about 0.0005:1 to about 0.5:1, and preferably from about 0.0005:1 to about 0.10:1. However, it should be understood that not all of the substance may become covalently bound to the particles. In fact, a minor amount may be adsorbed, and some may not be bound at all. One skilled in the art could readily perform tests to determine the amount of substance bound to the particles.

Mixing of substance and particles is carried out at a temperature of from about 20° to about 37° C. for from about 2 to about 30 hours. The length of time will vary with the temperature, particular reactive groups on the particles, particular biologically active substance and the desired coverage. Any suitable buffer can be used, but 2-(N-morpholino)ethanesulfonic acid and N-(2-hydroxyethyl)-piperazine-N'-(3-propanesulfonic acid) are preferred. The details of a representative procedure for making a reagent are shown in Examples 1 to 3 below.

It is desired that the biologically active substance be present in the reagent in an amount of from about 0.00025 to about 30%, and preferably from about 0.0005 to about 18% by weight of the polymer particles. As noted above, not all of the substance mixed with the particles may become bound. Hence, usually an excess of substance is mixed with the particles than actually is covalently bound.

Where the reactive groups on the particles are carboxy groups, an activating agent is used for attachment according to the teaching of U.S. Pat. No. 4,181,636 (noted above), EP-A-0 308 235 (noted above) and U.S. Ser. No. 389,390 (filed Aug. 3, 1989 by Scensny and Chen).

In the analytical or diagnostic methods of this invention, the reagents can be used to detect any specific binding ligand for which there is a receptor molecule. The biologically active substance in a reagent of this invention can be specifically reactive with either the ligand or its receptor. Ligand detection can be carried out in solution or dry form (described below) using test specimens of aqueous fluids (such as biological fluids), or solutions of tissue or cellular materials, and can be quantitative, qualitative or both. In particular, the invention can be used to assay biological fluids of animals, humans or plants, but preferably fluids of humans including whole blood, sera, plasma, lymph, bile, urine, spinal fluid, sputum, lacrimal fluid, perspiration, stool secretions, cellular fluids, tissue cultures, swab specimens, vaginal secretions and semen. It is also possible to assay fluid preparations of human or animal tissue such as skeletal muscle, heart, kidney, lungs, brains, bone marrow or skin.

The ligand can be a drug, hormone, an antigenic material (lipopolysaccharide or protein) or antibody which has one or more sites for complexation with one or more of the same or different receptor molecules. In immunoassays of this invention, the ligand can be a drug (such as digoxin, phenobarbital, phenytoin, gentamicin, theophylline and carbamazepine), hormone (such as thyroid stimulating hormone, human chorionic gonadotropin, leutinizing hormone, thyroxine and triiodothyronine), retroviral component or an antibody to the retrovirus (such as an HIV-I component or its antibody), bacterial infectious agents or components thereof or antibodies thereto (such as Streptococcus A antigen, Chlamydial or Gonococcal antigen or antibody), viruses or components thereof (such as hepatitis, cytomegalo-virus or herpes antigen) or antibodies thereto, cancer-producing agents, or C-reactive protein. The ligand can also be biotin or a derivative thereof, and the receptor is avidin or a derivative thereof.

In other embodiments, the ligand can be a nucleic acid (usually in single-stranded form), the amount or presence of which is detected using a complementary single-stranded nucleic acid as the receptor molecule. There are many various assay formats for nucleic acid detection, all of which are readily apparent to one skilled in the art. Detection of HIV-I DNA, $\beta$-globin DNA or cytomegalo-virus DNA is of particular interest in the practice of this invention.

In general, a method for the determination of a specific binding ligand comprises:

A. forming a water-insoluble specific binding complex of a specific binding ligand of interest, or a receptor therefor, with a reagent comprising:
   (I) a water-insoluble, nonporous particle as described above, and
   (II) a biologically active substance covalently attached to the particle through the reactive groups,
   the substance being specifically reactive with either the ligand or with a receptor therefor, and
B. detecting the presence of the complex as an indication of the presence or amount of the ligand in the specimen.

In one embodiment, the reagent can be used in competitive binding assays for determination of a specific binding ligand. A solution assay is one in which the reagents are used in a suspension of reagent and test specimen suspected of containing the ligand of interest. Either bound (that is, complexed) or unbound (that is, uncomplexed) materials can be determined in the assay. Physical separation of bound and unbound materials, if desired, can be carried out using any suitable separation technique. In using analytical elements (described below), either vertical or horizontal separation can be used. Bound ligand can be determined using light scattering, turbidimetric, radiometric or spectrophotometric techniques as are known in the art.

In a competitive binding assay, the reagent is generally present in a concentration which depends upon the amount of immunological species (that is, receptor) on the polymeric particles and the ligand of interest. A ligand analog (ligand which is detectably labeled) is also used so there is a competition between ligand and ligand analog for a known amount of receptor available for reaction. The assay is generally carried out by physically contacting and mixing the reagent, ligand analog and test specimen in a suitable container so that complexation occurs. Incubation may be used to promote complexation and any chemical or biological reactions (such as dye formation) needed for detection of the complexes.

More particularly, the ligand is an immunological species and the reaction of ligand and receptor therefor forms an immunological complex which is detectable once water-soluble (uncomplexed) materials are removed from the complex (for example, by filtration or centrifugation) to indicate the presence or absence of the species in the specimen.

The methods of this invention can also be carried out using dry analytical elements. The simplest element can be composed of a substrate (preferably absorbent or fluid permeable), for example, a thin sheet of a self-supporting absorbent or bibulous material such as a filter paper or paper strip. This substrate has one or more reaction zones for chemical, biological or specific binding reactions to occur therein. The reagent of this invention is present in at least one of these zones. Other optional zones can include other reagents, such as dyes, dye-providing compounds, scavengers, antioxidants, enzyme substrates or buffers and other materials readily apparent to one skilled in the art. Such elements are known in the art as test strips, analytical elements, slides or dip sticks.

Absorbent materials useful in preparing the elements can include cellulosic materials (such as porous papers), porous polymeric films, mats of glass fibers, woven or nonwoven fabrics and other materials known to one skilled in the art. Preferred substrates are porous spreading layers as described, for example, in U.S. Pat. No. 3,992,158 (issued Nov. 16, 1976 to Przybylowicz et al), U.S. Pat. No. 4,258,001 (issued Mar. 24, 1981 to Pierce et al), U.S. Pat. No. 4,292,272 (issued Sep. 29, 1981 to Kitajima et al) and U.S. Pat. No. 4,430,436 (issued Feb. 7, 1984 to Koyama et al).

Preferred elements can include one or more superposed fluid-permeable layers, all of which are superposed on a nonporous, fluid impermeable support (which can be transparent or not) composed of a suitable polymeric, cellulosic or metallic material. The layers can be used for various purposes, such as for reaction zones, subbing zones, reagent zones, barrier zones, radiation-blocking zones and other uses well known in the art. Where desired, reagents and buffers can move among the layers for the desired reactions to carry out the assay and provide a detectable product and separation of bound and unbound materials. Other components of analytical layers are described, for example, in U.S. Pat. No. 4,042,335 (issued Aug. 16, 1977 to Clément), U.S. Pat. No. 4,132,528 (issued Jan. 2, 1979 to Eikenberry et al), U.S. Pat. No. 4,144,306 (issued Mar. 13, 1979 to Figueras), U.S. Pat. No. 4,670,381 (issued Jun. 2, 1987 to Frickey et al) and EP-A-0 253 581 (published Jan. 2, 1988).

While it is preferred that the reagent of this invention be incorporated into an element for use, this is not critical because the reagent can be added to the element at the time of the assay along with the test specimen. Preferably, however, the ligand analog and reagent of this invention (containing the appropriate receptor) are located within the element in different zones so they will not complex prematurely.

In one preferred embodiment of this invention, an analytical element comprises a nonporous support, having imposed thereon, in order and in fluid contact, a reagent layer containing one or more reagents for providing a detectable signal in the assay,
a water-soluble layer containing an enzyme-labeled analog of a ligand of interest, and
a porous spreading layer containing the reagent of this invention composed of a receptor (for example, an antibody) for the ligand of interest.

Preferably, the ligand analog is labeled with a enyzme, such as one described below, the ligand is an antigenic material, hormone, hapten or drug, and the receptor is the corresponding antibody. Such elements are particularly useful for the determination of carbamazepine, thyroxine, phenobarbital, phenytoin or digoxin. Most preferably, they are useful for the determination of phenobarbital, carbamazepine, phenytoin or digoxin.

A variety of different elements, depending upon the method of assay, can be prepared according to this invention. They can be configured in a variety of forms, including elongated tapes of any desired width, sheets, slides or chips.

The solution or dry assay of this invention can be manual or automated. In general, in the use of dry elements, analyte determination is made by taking the element from a supply roll, chip packet or other source and physically contacting it with a sample of test specimen so the specimen and reagents within the element become mixed in one or more test zones. Such contact can be accomplished in any suitable manner, for example, by dipping or immersing the element into the sample or, preferably, by applying a drop of the specimen to the element with a suitable dispensing means. Wash fluids can also be used in the assay, for example as described in U.S. Pat. No. 4,517,288 (issued May 14, 1985 to Giegel et al).

Assay results are generally determined by observing detectable spectrophotometric changes in the element either visually or with suitable detection equipment.

Another embodiment of this invention is what is known in the art as agglutination assays whereby a ligand is complexed with the reagent of this invention to form a detectable agglutination or clumping of the particles. The resulting agglutination can be detected in a variety of ways, for example visually or with suitable light scattering detection equipment. Representative agglutination techniques are described, for example, in U.S. Pat. No. 4,419,453 (issued Dec. 6, 1983 to Dorman et al), U.S. Pat. No. 4,808,524 (issued Feb. 28, 1989 to Snyder et al), U.S. Pat. No. 4,828,978 (issued May 9, 1989 to Warren III et al) and U.S. Pat. No. 4,847,199 (issued Jul. 11, 1989 to Snyder et al).

Agglutination assays are preferably carried out using reagents of the present invention which are detectably labeled in some manner, such as with a radioisotope in the particle or in the biologically active substance attached thereto, or with a colorimetric or fluorometric dye associated with the particle. Most preferably, a dye is within the interior of the particle, that is away from its surface so as to not interfere with the attachment of a biologically active substance or its complexation. Such particles can be core-shell particles having the dye within a core polymer while the shell copolymer is free of dye. This feature and methods of making such particles are described in more detail in U.S. Pat. No. 4,808,524 (noted above) and in U.S. Ser. No. 098,583 (filed Sep. 18, 1987 by Sutton et al), now U.S. Pat. No. 4,997,772. In core-shell polymer particles, the shell copolymer has a composition like that described herein (that is, with the necessary reactive groups and polyoxyalkylene side chains), but the core polymer can be different and need not have such groups or side chains.

A method for the determination of an immunological species comprises:
A. contacting a specimen suspected of containing an immunological species with a reagent of this invention having a receptor for the species, to form a water-insoluble immunological complex of the species with the receptor, and
B. after separating uncomplexed materials from the complex, detecting the presence of the complex as an indicator of the presence or amount of the immunological species in the specimen.

The immunological species can be an antigenic material and the receptor an antibody therefor. Alternatively, the immunological species can be an antibody and the receptor an antigenic material specific therefor. Still again, the immunological species can be an antibody and the receptor an antibody specific therefor.

In still another embodiment, the reagent of this invention can be used in immunometric assays (often called "sandwich" assays). In such assays, the ligand of interest is complexed with two or more receptor molecules (the same or different), one of which is insolubilized or capable of being insolubilized (such as through an avidin-biotin bond), and the other being water-soluble and appropriately labeled (such as with a radioisotope, enzyme, chemiluminescent moiety or other marker known in the art). For example, a sandwich assay for a ligand such as human chorionic gonadotropin (hCG) can be carried out with a reagent of this invention having antibodies to the hormone in combination with enzyme-labeled antibodies to hCG which will complex at different epitopic sites than the reagent antibodies. The resulting sandwich complex is insoluble, detectable and separatable from uncomplexed materials (such as with a microporous membrane). In a preferred embodiment, the reagent of this invention has a receptor for the ligand of interest and is immobilized on the membrane. Sandwich assays are well known in the art, including GB-A-2,074,727 (published Nov. 4, 1981) and U.S. Pat. No. 4,486,530 (issued Dec. 4, 1984 to David et al), and references noted therein.

Preferably, in the sandwich assays, either prior to, simultaneously with or subsequently to the formation of the water-insoluble complex with the reagent of this invention, the ligand of interest is reacted with a water-soluble specific binding component specifically reactive therefor.

Other ligands which can be detected in sandwich assays according to this invention include, but are not limited to, Streptococcal antigens, antigens extracted from microorganisms associated with periodontal diseases, hepatitis antigens, HIV-I and other retroviral antigens.

In one embodiment of the sandwich assay, the reagent of this invention is directly reacted with the ligand of interest, for example, where the ligand is an antigen, and the reagent has antibodies thereto. In another embodiment, however, the reagent is complexed with the ligand indirectly, that is, through an intermediate linking moiety. One example of this is shown in U.S. Pat. No. 4,870,007 (issued Sep. 26, 1989 to Smith-Lewis), where complexation is through an avidin-biotin bond.

Another embodiment of this invention is what is known as a hybridization assay wherein a targeted nucleic acid is detected using complementary probes, one of which is suitably labeled, and the other is immobilized, or capable of being immobilized. The reagent of this invention can be used as an immobilization probe in such assays. Examples of hybridization assays are shown, for example, in U.S. Pat. No. 4,358,535 (issued Nov. 9, 1982 to Falkow et al) and U.S. Pat. No. 4,486,539 (issued Dec. 4, 1984 to Ranki et al). These reagents can also be used as capture probes after what is known in the art as polymerase chain reaction amplification, for example, as described in more detail in U.S. Pat. No. 4,683,195 (issued Jul. 28, 1987 to Mullis et al), U.S. Pat. No. 4,683,202 (issued Jul. 28, 1987 to Mullis) and U.S. Ser. No. 273,779 (filed Nov. 21, 1988 by Burdick et al), now abandoned.

In particular, a method for the detection of a nucleic acid comprises:
A. forming a water-insoluble hybridization product between a nucleic acid of interest, with a reagent of this invention having an oligonucleotide covalently attached to the particle through the reactive group, the oligonucleotide being substantially complementary to the nucleic acid of interest, and B. detecting the presence of the hybridization product as an indication of the presence or amount of the nucleic acid of interest.

In preferred hybridization assays, the nucleic acid of interest is amplified using polymerase chain reaction (known in the art) with suitable reagents (for example, DNA polymerase, dNTPs, primers) prior to capture with the reagent of this invention. HIV-I DNA, cytomegaloviral DNA and β-globin DNA are readily detected using amplification and detection according to this invention. In one embodiment, one of the primers is biotinylated, and detection of the amplified nucleic acid is accomplished using a conjugate of avidin and an enzyme. The hybridized product can be captured using the reagent which may be attached to or localized on a substrate of some type, including a microporous substrate such as a membrane, or a compartment of a self-contained reaction pouch.

The analytical, sandwich and hybridization assays of this invention can be carried out using suitable equipment and procedures whereby complexed or hybridized product is captured or separated from uncomplexed materials by filtration, centrifugation or other means. Preferably, such assays are carried out using disposable test devices which contain microporous filtration membranes (for example those commercially available from Pall Corp.). Representative test devices are shown in U.S. Pat. No. 3,825,410 (issued Jul. 23, 1974 to Bagshawe), U.S. Pat. No. 3,970,429 (issued Jul. 20, 1976 to Updike) and U.S. Pat. No. 4,446,232 (issued May 1, 1984 to Liotta). Particularly useful test devices are shown in U.S. Ser. No. 98,248 (filed Sep. 18, 1987 by Hinckley et al), and are commercially available as SURECELL ™ test devices (Eastman Kodak Co.). Self-containing pouches are described in U.S. Ser. No. 306,954 filed Feb. 3, 1989 by Findlay et al.

The analytical separation method of this invention can be used to isolate one or more analytes of interest from a mixture of biological materials. Thus, the reagent of this invention (or several reagents having different substances attached to particles) is generally placed in a column through which a fluid containing the mixture of biological materials is poured, allowing the reagent to extract from the fluid those materials one wants to isolate. This may be useful in the purification of nucleic acids, enzymes, carbohydrates, proteins, lipids, vitamins, steroids, antibodies, peptides or hormones. This procedure is also known as affinity chromatography.

Affinity chromatography can also be used to concentrate dilute solutions of proteins in order to remove denatured forms thereof from refined proteins, and in the separation and resolution of protein and peptide components which have originated in specific chemical modifications.

Another use of this method is to purify nucleic acids, such as those resulting from polymerase chain reaction amplification, as described, for example in U.S. Ser. No. 475,068 (filed Feb. 5, 1990 by Oakes et al) as a continuation-in-part of U.S. Ser. No. 325,311 (filed Mar. 17, 1989 by Oakes et al), now abandoned.

The reagent of this invention can be supplied for any of the described methods as a single material, or it can be supplied in an analytical element as described above, or yet again in combination with other reagents, test devices and equipment in a diagnostic test kit. For the purification method, the reagent can also be supplied in an affinity chromatography column.

Specifically, a kit for a hybridization assay includes a reagent of this invention having an oligonucleotide complementary to the nucleic acid of interest, and one or more other reagents (for example, labeled probe or polymerase chain reaction reagents), solutions (such as wash or extraction solutions) or articles (such as pipettes, filters, test devices or test vessels) needed for the assay.

In another embodiment, a kit useful for determination of a ligand (for example immunoassay, sandwich assay, diagnostic test or competitive binding assay) includes the reagent of this invention, and one or more other reagents, solutions or articles needed for such an assay (such as ligand analog, labeled receptor, dye-providing compositions, substrates, wash solutions, filters, test devices, extraction reagents and others known in the art).

In the analytical purification method of this invention, the reagent in the chromatography column captures one or more of the substances in the mixture of substances poured through the column.

In one embodiment, the predetermined substances are captured by the reagent, the original eluent is discarded and the captured substances are removed from the column using a solvent which alters the binding characteristics of the substances so they can be uncomplexed. Such solvents include buffers which alter the pH, salt solutions which alter the ionic nature of the complex or solutions containing a second species which will specifically bind to the reagent and replace the captured substance.

Alternatively, the predetermined substances captured by the reagent are discarded, and other chemical or biological materials remaining in the original eluent are collected.

The following examples are for illustrative purposes only, and not meant to limit the scope of the invention. All percentages are by weight, unless otherwise specified.

EXAMPLE 1

Preparation of Reagent Comprising an Antibody Attached to Polymeric Particles

This example illustrates the preparation of reagents of this invention having biological substances covalently attached to particles of copolymers described herein.

Particles of the following copolymers were prepared using reagents and procedures described in our copending U.S. Ser. No. 557,338, now U.S. Pat. No. 5,086,143:

A: Poly[styrene-co-m & p-(2-chloroethylsulfonylmethyl)styrene-co-ethylene dimethacrylate] (94.5:4.5:1 molar ratio, 0.66 μm average diameter), B: Poly[styrene-co-m & p-(2-chloroethylsulfonylmethyl)styrene-co-pentaethylene glycol mono methacrylate] (95.25:4.5:0.25 molar ratio, 1.1 μm average diameter), C: Poly[styrene-co-m & p-(2-chloroethylsulfonylmethyl)styrene-co-pentaethylene glycol mono methacrylate] (94.5:4.5:1 molar ratio, 0.53 μm average diameter)

D: Poly[styrene-co-m & p-(2-chloroethylsulfonylmethyl)styrene-co-pentaethylene glycol mono methacrylate] (90.5:4.5:5 molar ratio, 0.51 μm average diameter)

E: Poly[styrene-co-m & p-(2-chloroethylsulfonylmethyl)styrene-co-decaethylene glycol mono methacrylate-co-divinyl benzene] (93.5:4.5:1:1 molar ratio, 1.8 μm average diameter)

Polymers B–E are within the scope of this invention while Polymer A is not.

The particles were treated under the same conditions. Reaction dispersions were prepared comprising either $^{125}$I-bovine gamma globulin (0.3 mg) or anti-phenobarbital antibody (0.3 mg) and particles (30 mg dry weight) in 3-[4-(2-hydroxyethyl)-1-piperazinyl]propanesulfonic acid buffer (0.1 molar, pH 8.5), sufficient to bring the final volume to 1.5 ml.

Aliquots of the dispersions (containing 30 mg polymer dry weight) were placed in 2 ml microfuge tubes, and buffer was added to bring the volume in each tube to 1.5 ml. The particles were centrifuged 6 minutes at 13,000 rpm and the supernatant discarded. The particles were then resuspended with buffer (1.35 ml for the labeled globulin and 1.385 ml for the antibody). An aliquot of protein (0.15 ml for the labeled globulin or 0.115 ml for the antibody) was added to each tube, the tubes were capped and rotated end-over-end for 24 hours. An aliquot of the labeled globulin mixture was reserved for analysis of radioactivity.

The reactions of protein to particle surface were quenched by the addition of bovine serum albumin solution (0.3 ml at 100 mg/ml). The tubes were rotated end-over-end for an additional four hours, and the reaction mixtures were centrifuged for 6 minutes. Aliquots of the supernatant were reserved for analysis of radioactivity or for analysis by a total IgG enzyme-labeled immunoassay. The particles were resuspended in buffer (1 ml). This step was repeated once for the labeled globulin, and three times for the antibody. The final suspension of the labeled globulin reagent was 1.5 ml in sodium dodecyl sulfate (1%) and sodium phosphate buffer (0.2 molar, pH 7.4). The final suspension for the antibody reagent was 1.8 ml in phosphate buffered saline solution and merthiolate preservative (0.02%).

The supernatants from the antibody reagent were analyzed for total antibody concentration by immunoassay, and the amount of antibody bound to the particles was then calculated.

The $^{125}$I-labeled globulin reagent in sodium dodecyl sulfate was analyzed for radioactivity and rotated end-over-end for 24 hours at 37° C. to remove protein not covalently bound to the particles. The mixtures were then centrifuged for 6 minutes. Aliquots of the supernatant were analyzed for radioactivity and the particles were resuspended in sodium dodecyl sulfate (1 ml). This was repeated once and the pellets were analyzed for radioactivity. The results are as follows:

| Polymer | mg/g Total Bound | mg/g Covalent Bound |
| --- | --- | --- |
| A | 8.8 | 8.7 |
| B | 6.3 | 6.2 |
| C | 5.2 | 4.8 |
| D | 0.69 | 0.31 |
| E | 1.1 | 0.68 |

These results indicate that covalent binding occurs on all of the particles used according to this invention (B–E). As compared with the reagent having particles A, the extent of total and covalent binding were modulated by the presence of comonomers having polyethylene oxide side chains.

The relative amounts of reactive anti-phenobarbital antibody in the preparations were determined in an assay in which serial dilutions of the antibody-particle reagent was mixed with a fixed amount of phenobarbital-glucose oxidase analog ($5 \times 10^{-10}$ molar). The immunological reaction was carried out for one hour at room temperature with constant agitation in phosphate buffered saline solution containing bovine serum albumin (0.1%). The amount of labeled analog remaining in the solution after centrifugation was determined and the theoretical number of binding sites required to bind 50% of the labeled antibody were calculated, The results are shown as follows:

| Polymer | mg/g Total Bound | nMolar Theoretical Binding Sites Required to Bind 50% of Labeled Analog |
| --- | --- | --- |
| A | 10 | 34 |
| B | 9.9 | 42 |
| C | 9.6 | 7.0 |
| D | 5.1 | 57 |
| E | 5.7 | 10 |

These results indicate that all of the reagents prepared according to this invention contained reactive anti-phenobarbital antibody, The reagents prepared using polymers C and E gave the best results since far fewer theoretical binding sites were required to bind the same amount of labeled analog, This implies a higher fraction of immobilized binding sites are active on these particles than on the other particles,

EXAMPLES 2 AND 3

Preparation of Reagent Having Antigen Attached to Particles

These examples illustrate the covalent attachment of HIV-I antigen to polymeric particles to provide a reagent of this invention. These reagents are used in the assays of Example 6 below.

For Example 2, polymeric particles of poly[styrene-co-m & p-(2-chloroethylsulfonylmethyl)styrene-co-pentaethylene glycol mono methacrylate-co-m & p-divinylbenzene] (93.5:4.5:1:1 molar ratio) were prepared according to the procedures described in detail in U.S. Ser. No. 557,388, now U.S. Pat. No. 5,086,143, (filed on even date herewith by ourselves, noted above). The average particle size was about 1.67 μm.

Similarly, for Example 3, particles of poly[styrene-co-m & p-(2-chloroethylsulfonylmethyl)styrene-co-decaethylene glycol mono methacrylate-co-m & p-divinylbenzene] (93.5:4.5:1:1 molar ratio) were prepared.

Antigen from HIV-I viral particles was obtained in the following manner: Hut 78 cell line was cultured in Roswell Park Memorial Institute-1640 medium in the presence of 10% bovine serum albumin and gentamycin (50 μg/ml). The cell density was maintained at about $10^5$–$10^6$ cells/ml, and the cells were subcultured by the addition of fresh medium to maintain this density. The viral particles were isolated in a closed-system stainless steel filtration/concentration apparatus by pooling the cultures to be harvested in a holding tank which permits the cell culture fluid to be pumped through a filter housing fitted with a 0.45 μm filter. This first filtration step removed whole cells and cell debris. The cell-free supernatant was then pumped through a second filter housing fitted with a 0.2 μm filter in order to eliminate any residual cell debris not removed by the 0.45 μm filter. The second supernatant was pumped through a concentration cassette fitted with a 100,000 dalton cut-off membrane to concentrate the preparation to a suitable volume. The crude viral particles thus obtained were pelletized by centrifugation for two hours at about 50,000×g and resuspended in about 40 ml of a buffer solution [pH 7.8, 0.01 molar tris(hydroxymethyl)aminomethane hydrochloride, 0.01 molar sodium chloride, 0.001 molar ethylenediaminetetraacetic acid] layered over a 1300 ml linear 22–65% sucrose gradient in the buffer with a standard zonal rotor and ultracentrifuged overnight at about 30,000×g. The gradient was fractionated into about 110 fractions (12 ml each) and all fractions with densities between 1.14 and 1.18 g/ml were pooled, diluted 3- to 4-fold with the buffer and centrifuged at about 50,000×g for two hours to recover the purified HIV-I viral particles. The particles were then suspended in 10 ml of a solution containing 0.6 molar potassium chloride and 0.5% of a nonionic octylphenoxy polyethoxyethanol surfactant, sonicated with three 5-second bursts, incubated for one hour at 37° C. and centrifuged at 80,000×g for one hour to remove debris. The solubilized HIV-I preparation was then extracted twice with an equal volume of anhydrous ether and the resulting aqueous phase was used as the source of HIV-I antigen in this example.

Particles of each polymer (13.5 mg dry weight) identified above were dispersed in sodium borate buffer (3 ml, 0.05 molar, pH 8.5) and combined with HIV-I antigen (0.15 mg dry weight) as described above in a polypropylene centrifuge tube. Reaction of antigen with the reactive groups on the particle surface was allowed to continue for 18-24 hours at room temperature using end-over-end rotation.

At the end of the reaction time, the tubes were centrifuged to separate the insoluble reagents, The reagent pellets were washed in glycine buffer (0.1 molar, pH 8.5) and resuspended to a final volume in glycine buffer (3 ml), yielding about 0.3% solid suspension of each reagent.

EXAMPLE 4

Preparation of Reagent Having Antibodies to Phenytoin

This example illustrates the preparation of a reagent of this invention having anti-phenytoin antibodies attached to polymeric particles.

For this example, polymeric particles composed of poly[styrene-co-m& p-(2-chloroethylsulfonylmethyl)styrene-co-pentaethylene glycol mono methacrylate-co-divinylbenzene] (93.5:4.5:1:1 molar ratio, 1.67 μm average particle diameter) were prepared according to the procedures described in our copending U.S. Ser. No. 557,338, now U.S. Pat. No. 5,086,143.

An aliquot (6.15 ml at 16.26% solids) was placed in a 30 ml centrifuge tube and centrifuged at 8000 rpm for 30 minutes. The supernatant was discarded and the particles were redispersed in 3-[4-(2-hydroxyethyl)-1-piperazinyl]propanesulfonic acid buffer (19.85 ml, 0.1 molar, pH 8.5). A solution of anti-phenytoin antibody (4 ml at 2.47 mg/ml) was added and the reaction mixture was stirred at room temperature for 18.5 hours. An aliquot of bovine serum albumin solution was added (10 ml at 10%), and the reaction mixture was stirred for 4 hours at room temperature. The mixture was then centrifuged at 8000 rpm for 30 minutes. An aliqout (2 ml) of the supernatant was reserved for analysis of unbound antibody. The pellet was washed by resuspending in phosphate buffered saline solution (25 ml, pH 7.4) and centrifuging at 8000 rpm for 30 minutes. The pellet was washed three times. The final resuspension was in phosphate buffered saline solution (10 ml) containing merthiolate (0.02%). The resulting reagent was stored at 4° C. until use.

EXAMPLE 5

Analytical Element and Its Use To Determine Phenytoin

This example demonstrates the preparation of an analytical element of this invention and its use in a competitive binding assay to detect the drug phenytoin.

The element was prepared using known technology to have the following structure:

|   |   | Coverage (g/m$^2$) |
|---|---|---|
| Spreading Layer | Reagent of Example 4 | 0.1 |
|  | Particles of poly[m- & p-vinyltoluene (64:36)-co-methacrylic acid) (98:2 weight ratio) (30 μm) | 129 |
|  | 4,5-bis-(4-dimethylaminophenyl)-2-(4-hydroxy-3,5-dimethoxyphenyl)imidazole leuco dye | 0.2 |
|  | Poly(methyl acrylate-co-sodium 2-acrylamido-2-methylpropanesulfonate-co-2-acetoacetoxyethyl methacrylate) (90:4:6 weight ratio) | 3 |
|  | 3-(4-morpholino)propane sulfonic acid buffer (pH 7.2) | 0.2 |
|  | KELZAN ™ xanthan gum (Kelco) | 0.065 |
|  | Dimethyl sulfoxide | 1.8 |
|  | 5,5-dimethyl-1,3-cyclohexanedione | 0.05 |
|  | ZONYL ™ FSN nonionic surfactant (DuPont) | 0.054 |
| Gelatin Layer | Hardened gelatin | 10 |
|  | 4'-hydroxyacetanilide | 0.15 |
|  | Potassium phosphate buffer | 0.68 |
|  | TRITON ™ X-100 nonionic surfactant (Rohm & Haas) | 0.02 |
|  | Poly(ethylene terephthalate) Support |  |

A series of aqueous solutions containing phenytoin standards and a horseradish peroxidase-labeled phenytoin analog in phosphate buffered saline solution (pH 7.4) containing bovine serum albumin (1%) was prepared. The concentration of phenytoin varied from zero to $10^{-4}$ molar. The concentration of the analog was 1 nmolar.

The series of phenytoin standards (10 μl aliquots) was spotted onto the spreading layers of a series of analytical elements. After 5 minutes incubation at 37° C., a wash solution (10 μl) comprising hydrogen peroxide (0.03%), sodium phosphate buffer (0.01 molar, pH 6.8), 4'-hydroxyacetanilide (5 mmolar) and diethylenetriaminepentaacetic acid (10 μmolar) was added to wash unbound complex away from the center of the area to which the phenytoin standards had been applied, and to initiate dye formation. After about 1 minute, the change (rate) in reflection density ($\Delta D_R$) was measured at the center of the area at 680 nm at 37° C. over 30 seconds. The results are shown below in Table I.

TABLE I

| Phenytoin Concentration (molar) | Rate ($\Delta D_R$/Min.) |
|---|---|
| $10^{-4}$ | 0.0101 |
| $10^{-5}$ | 0.0246 |
| $10^{-6}$ | 0.0606 |
| $10^{-7}$ | 0.0786 |
| $10^{-8}$ | 0.0705 |
| 0 | 0.0719 |

EXAMPLE 6

Determination of HIV-I Antibodies in Biological Specimen

This example illustrates how the present invention can be used as a diagnostic assay for the determination of an infectious agent in a biological specimen. In this instance, HIV-I antibodies are detected in human serum using the reagents described in Examples 2 and 3 above.

Materials

SURECELL TM disposable test devices (Eastman Kodak Co.) containing uncoated LOPRODYNE TM micorporous filtration membranes (Pall Corp.) in each test well were prepared for use in the assays. Solutions of the reagents of Examples 2 and 3 (50 μl of each) having HIV-I antigen covalently attached as described in Example 4 above, polyacrylamide (75 μg) and FLUORAD TM FC-135 nonionic fluorinated surfactant (1 μg, 3M Company) were added to one test well of each test device, respectively. A separate solution of each corresponding polymer (without antigen, 50 μl), polyacrylamide (75 μg) and FLUORAD TM FC-135 nonionic fluorinated surfactant (1 μg) was added to a second test well of each device to provide a negative control. In some cases, glycine buffer (10 μl, pH 8.5) was added to the test wells to wet the membranes. The reagents and polymers were allowed to dry on the membranes for about 15 hours).

Control test devices were similarly prepared with the following polymers and reagents prepared therefrom, using the procedures shown in Examples 2 and 3:

Control A: poly[styrene-co-m & p-(2-chloroethylsulfonylmethyl)styrene-co-2-hydroxyethyl acrylate] (93.5:4.5:1 molar ratio), 1.73 μm average particle size and 12.34% solids after dialysis, and Control B: poly[styrene-co-m & p-(2-chloroethylsulfonylmethyl)styrene] (94.5:4.5 molar ratio), 2.1 μm average particle size and 8% solids after dialysis.

A diluent composition was prepared from succinylated casein (1%), gum arabic (1%) and TWEEN TM 20 nonionic surfactant (0.05%) in tris(hydroxymethyl)aminomethane hydrochloride buffer (100 mmolar, pH 8.0). Succinylated casein was prepared by reacting casein with an equal weight of succinic anhydride for four hours at 25° C. in phosphate buffer (0.5 molar, pH 8.5), then purifying the product by dialysis.

The wash solution contained sodium decyl sulfate (2.4%) in sodium dihydrogen phosphate buffer (0.1 molar, pH 8.0).

A conjugate of horseradish peroxidase with rabbit anti-human antibodies was prepared by mixing 1.6 μg of peroxidase per ml of the diluent noted above with the antibodies using known procedures and commercially available starting materials.

A dye-providing composition was prepared from a leuco dye solution having 2-(4-hydroxy-3,5-di-methoxyphenyl)-4,5-bis(4-methoxyphenyl)imidazole (0.1% solution) and poly(vinylpyrrolidone) (20%) in sodium phosphate buffer (5 mmolar). This solution was then added to a solution containing hydrogen peroxide (10 mmolar), 4'-hydroxyacetanilide electron transfer agent (5 mmolar) and diethylenetriamine-pentaacetic acid chelating agent (10 μmolar) in sodium phosphate buffer to produce a final concentration of 1% poly(vinylpyrrolidone) and 0.005% leuco dye.

Assays

Each of the reagents of this invention (from Examples 2 and 3) and the Control A and B reagents were used to detect HIV-I antibodies in human serum samples that were identified as positive for HIV-I antibodies using Western Blot testing.

Test samples were mixed with peroxidase-labeled antibodies to give a high concentration HIV-I serum sample (1:80 dilution) or a low concentration HIV-I serum sample (1:5000 dilution) as follows: For the 1:80 dilution sample, HIV-I positive serum (25 μl) was diluted to 2 ml with labeled antibodies in diluent. For the 1:5000 diluted sample, HIV-I positive serum (25 μl) was diluted to 1.6 ml with a HIV-I negative serum, and then 25 μl of this mixture was diluted to 2 ml with labeled antibodies in diluent.

The diluted serum samples (270 μl/well) were added to the specimen and negative control test wells and allowed to drain through. The wash solution (about 270 μl) was added to each test well, allowed to drain, washed again (60 μl) and allowed to drain a second time.

The leuco dye solution (50 μl) was added, and after two minutes, dye formation in the test wells was stopped. Dye formed was visually measured by grading from 0 to 10 with 0 representing no dye density and 10 representing highest dye density. The results of the assay are shown in Tables II and III below. Table II shows the dye readings formed using the reagents, whereas Table III shows the dye readings provided by the respective polymers alone (no antigen) in the Control test devices.

It is evident from Table II that all of the reagents show desired sensitivity for the antibodies (although the reagent of Example 3 had weak sensitivity at the greatest dilution). However, from Table III, it is apparent that dye formation from nonspecific binding was highest for both assays using Control reagents, and particularly for the assay using Control B at the highest dilution. Both assays using the reagents of Examples 2 and 3 showed desirably low dye formation from nonspecific binding.

TABLE II

| | REAGENT | | | |
|---|---|---|---|---|
| Serum Dilution | Example 2 | Example 3 | Control A | Control B |
| 1:80 | 9 | 5.3 | 9 | 8 |
| 1:5000 | 5.3 | 0.7 | 4.7 | 5 |

TABLE III

| Serum Dilution | Example 2 Polymer | Example 3 Polymer | Control A Polymer | Control B Polymer |
|---|---|---|---|---|
| 1:80 | 0.2 | 0.2 | 0.3 | 0.3 |
| 1:5000 | 0 | 0 | 0.3 | 0.5 |

In addition, three serum samples known to be negative for HIV-I antibodies according to Western blot testing were assayed according to this invention to determine the amount of nonspecific binding that might occur with the reagents of Examples 2 and 3 and Controls A and B.

This test is an indication of the likelihood of false positives with each reagent. The reagents were diluted 1:80 with the diluent composition. The results of the assays are shown in Table IV below. It is apparent that the assay using the Control B reagent showed the most nonspecific binding for most serum samples. The assay using the Control A reagent was generally better than that using the Control B reagent. Examples 2 and 3 were as good as or better than the assay using the Control B reagent for all serum samples. The assay using the Control A reagent was better than Examples 2 and 3 in some cases, but looking at this data with the data of Table III, the Control A reagent does not provide consistently improved results with respect to nonspecific binding.

TABLE IV

| Serum Sample | REAGENT | | | |
|---|---|---|---|---|
| | Example 2 | Example 3 | Control A | Control B |
| 1 | 0 | 0.3 | 0.2 | 0.3 |
| 2 | 1.3 | 0.8 | 0.3 | 5 |
| 3 | 1 | 0.2 | 0.7 | 1.3 |

The invention has been described in detail with particular reference to preferred embodiments thereof, but it will be understood that variations and modifications can be effected within the spirit and scope of the invention. Moreover, all patents, patent applications (published or unpublished, foreign or domestic), literature references or other publications noted above are incorporated herein by reference for any disclosure pertinent to the practice of this invention.

We claim:

1. A method for the detection of a nucleic acid comprising:
    A. forming a water-insoluble hybridization product between said nucleic acid of interest, with a reagent comprising:
        (I) a water-insoluble nonporous particle whose outer surface comprises a copolymer having recurring units derived by polymerization from:
            (a) at least about 0.5 mole % of one or more ethylenically unsaturated polymerizable monomers having reactive groups which are, directly or indirectly, capable of reaction with an oligonucleotide having an amino or sulfhydryl group,
            (b) from about 0.1 to about 20 mole % of one or more ethylenically unsaturated polymerizable monomers which are represented by the structure:

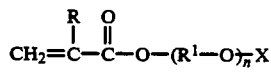

wherein R is hydrogen or methyl, $R^1$ is alkylene having 2 to 4 carbon atoms, X is hydrogen or acyl and n is 2 to 30, and
            (c) from about 60 to about 99.4 mole % of one or more ethylenically unsaturated oleophilic monomers which provide hydrophobicity to said copolymer, said monomers being selected from the group consisting of vinyl aromatics, acrylic end methacrylic acid esters and amides, butadiene, acrylonitrile, vinyl acetate, vinylbenzyl acetate, vinyl bromide, vinylidene chloride and crosslinkable monomers, and
        (II) said oligonucleotide covalently attached to said particle through said reactive groups, said oligonucleotide being complementary to said nucleic acid of interest, and
    B. detecting the presence of said hybridization product as an indication of the presence or amount of said nucleic acid of interest.

2. The method of claim 1 wherein said nucleic acid of interest is amplified using polymerase chain reaction prior to contact with said reagent.

3. The method of claim 1 wherein said nucleic acid of interest is HIV-I DNA, cytomegaloviral DNA or β-globin DNA.

4. The method of claim 2 carried out using a set of primers, one of which is biotinylated, and detection of the nucleic acid of interest is accomplished using an enzyme-avidin conjugate.

5. The method of claim 1 wherein said reagent is immobilized on a microporous membrane.

6. The method of claim 1 wherein said reagent is immobilized on a nonporous solid substrate.

7. The method of claim 1 wherein said copolymer has recurring units derived by polymerization from:
    about 1 to about 20 mole % of the monomers in (a),
    about 1 to about 20 mole % of the monomers in (b),
    and about 60 to about 98.5 mole % of the monomers in (c).

8. The method of claim 1 wherein $R^1$ is alkylene having 2 or 3 carbon atoms, and n is 2 to 20.

9. A kit for a hybridization assay for a nucleic acid of interest comprising:
    a. a reagent comprising:
        (I) a water-insoluble, nonporous particle whose outer surface, comprises a copolymer having recurring units derived by polymerization from:
            (a) at least about 0.5 mole % of one or more ethylenically unsaturated polymerizable monomers having reactive groups which are, directly or indirectly, capable of reaction with an oligonucletide having an amino or sulfhydryl group,
            (b) from about 0.1 to about 20 mole % of one or more ethylenically unsaturated polymerizable monomers which are represented by the structure:

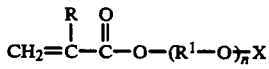

wherein R is hydrogen or methyl, $R^1$ is alkylene having 2to 4 carbon atoms, X is hydrogen or acyl and n is 2 to 30, and
            (c) from about 60 to about 99.4 mole % of one or more ethylenically unsaturated oleophilic monomers which provide hydrophobicity to said copolymer, said monomers being selected from the group consisting of vinyl aromatics, acrylic and methacrylic acid esters and amides, butadiene, acrylonitrile, vinyl acetate, vinylbenzyl acetate, vinyl bromide, vinylidene chloride and crosslinkable monomers, and
        (II) said oligonucleotide covalently attached to said particle through said reactive groups, said oligonucleotide being complementary to said nucleic acid of interest, and
    b. one or more additional reagents, solutions or equipment needed for said assay.

* * * * *